United States Patent [19]

Decker et al.

[11] 4,099,520
[45] Jul. 11, 1978

[54] BLOOD SAMPLING APPARATUS

[76] Inventors: Donald H. Decker, 1106 W. Bellbrook, Covina, Calif. 91722; William R. Davis, 6532 44th Northeast, Seattle, Wash. 98115; Duane W. Falleti, 2231 Enterprise Dr., Richland, Wash. 99352

[21] Appl. No.: 785,509

[22] Filed: Apr. 7, 1977

[51] Int. Cl.² .............................................. A61B 5/14
[52] U.S. Cl. .............................. 128/2 F; 128/DIG. 5; 128/216; 128/276
[58] Field of Search ............... 128/2 F, 218 R, 218 P, 128/218 PA, 218 NV, 215, 216, 224, 234, DIG. 5, 220, 221, 276

[56] References Cited

U.S. PATENT DOCUMENTS

| 3,776,218 | 12/1973 | Svensson | 129/2 F |
| 3,874,367 | 4/1975 | Ayres | 128/2 F |
| 3,890,955 | 6/1975 | Elliott | 128/2 F |
| 3,965,889 | 6/1976 | Sachs | 128/2 F |
| 4,057,050 | 11/1977 | Sarstedt | 128/2 F |

Primary Examiner—John D. Yasko
Attorney, Agent, or Firm—James E. Brunton

[57] ABSTRACT

An apparatus for the in viva acquisition of fluid samples from birds, fish, whales, and other mammals. The apparatus may also be used with equal proficiency for injecting fluids such as anesthetics, into the bird, mammal or other creature. When used in either manner, the apparatus is fully automatic. Once it is affixed to the animal, fluid samples can be taken or fluids injected while the animal freely moves about in its natural habitat at remote locations from the researcher.

13 Claims, 8 Drawing Figures

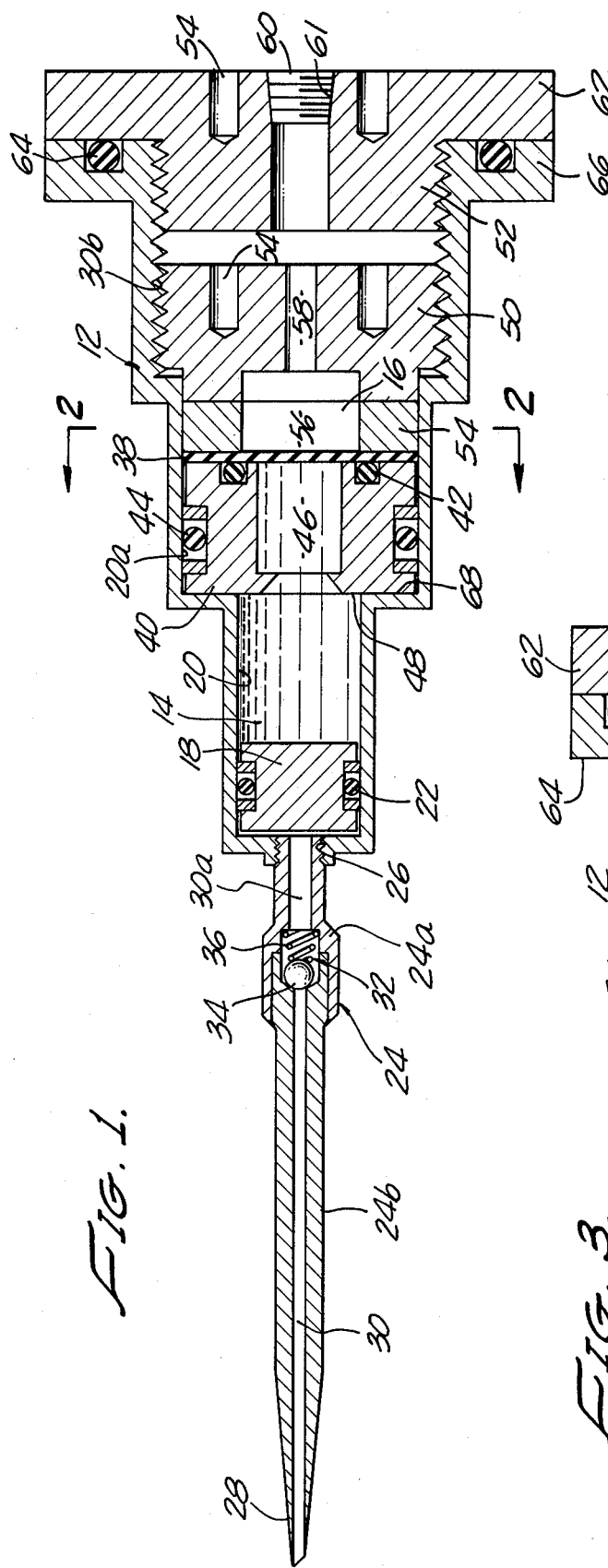
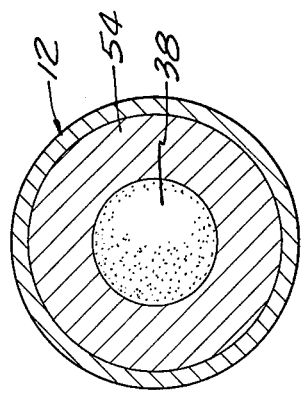
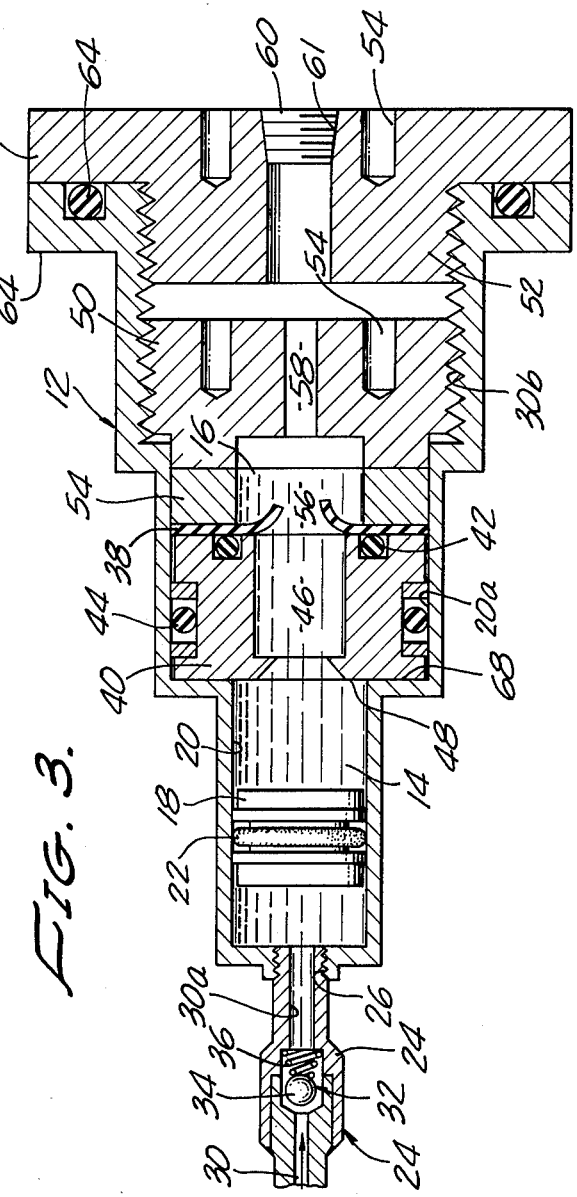

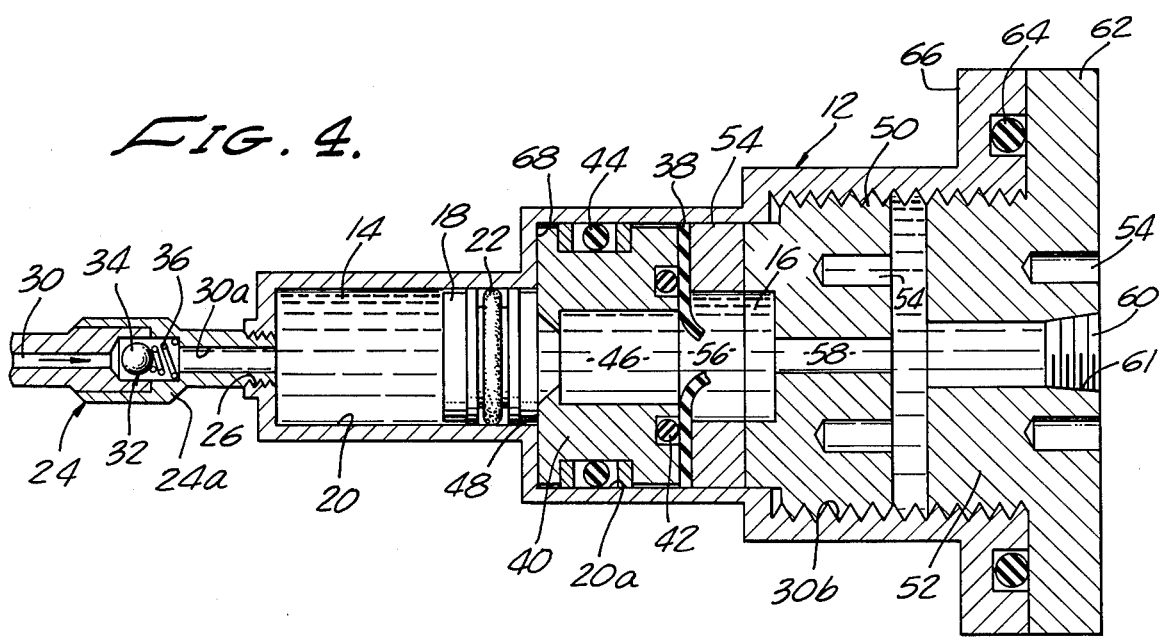

BLOOD SAMPLING APPARATUS

BACKGROUND OF THE INVENTION

1. Field of the Invention

The present invention relates to sampling devices for the in viva acquisition of fluid samples from animals.

2. Discussion of the Prior Art

Many types of apparatus have heretofore been suggested for acquiring samples of the body fluids of animals. Similarly, many types of devices have been suggested for injecting fluids into the body of animals. Almost without exception, however, such sampling and injection devices have been designed for use in controlled-environment laboratory-type conditions. For example, when it is desired to sample the blood, or other body fluid of a bird, whale, fish, or other wild creature, the creature is captured and placed into a laboratory-type environment. The samples are then taken when the animal is in other than its natural habitat. This technique severely limits the type of experimentation which can be undertaken. Additionally, samples taken when the animal is in an unnatural laboratory-type environment may provide inaccurate physiological data.

When attempts are made to use the prior art laboratory-type sampling apparatus in the field, numerous difficulties result. In the first place, most of the prior art equipment is highly sophisticated and is not designed to withstand use other than in controlled laboratory conditions. Such equipment frequently fails when exposed to the rigors of field operations. Secondly, the instrumentation, and particularly, its related operational support equipment is quite complicated, difficult to transport and poorly adapted for field set up.

The unique apparatus of the present invention effectively overcomes the aforementioned drawbacks of prior art devices. It is rugged in design and although useful under laboratory conditions, is specifically adapted to permit in vivos sampling of the wild creature while freely moving about in its environment. Once affixed to the mammal or other animal, the device is fully automatic so that samples may be taken at predetermined times and at locations remote from the researcher. The apparatus can be used either for acquiring samples, such as blood, or for injecting fluids, such as anesthetics, into the creature. When used, for example, in studies of acquatic mammals, accurate analyses can be made of cardiovascular parameters and metobolic rates for both shallow and deep diving mammals. Due to the novel manner in which the fluid sample is stored in the apparatus, an accurate analysis can be made of dissolved gases in the body fluid of the creature. The apparatus is highly versatile and, in addition to permitting accurate analysis of dissolved gases, enables analysis of lactic acid and organic phosphates to determine how the increase in concentration of these substances alters with depth.

When the apparatus is used for sampling blood, its unique design permits retrieval of the sample at slow expansion rates by means of a metering valve. This enables more accurate corpuscle counts to be obtained by reducing the potential for damaging blood cells.

The apparatus is of a simple design and permits the use of unsophisticated field-worthy support equipment. It is, nevertheless, extremely accurate in operation and embodies a minimum number of moving parts thereby increasing its reliability and reducing its temperature sensitivity.

The apparatus of the invention can be used with equal proficiency either for sampling body fluids or for injecting fluids into the creature. When used in the study of wild animals, for example, one device can be used as a sampler and another as an injector. With the sampler, the desired sample of body fluid can be obtained. With the injector, anesthetics can be automatically injected into the animal so that the sampler can readily be recovered.

Applicant is familiar with the following prior art patents which represent the closest art known to applicant and which serve to illustrate the novelty of the invention as described and claimed herein.

U.S. Pat. No. 3,568,663 — Phipps
U.S. Pat. No. 3,890,955 — Elliott
U.S. Pat. No. 3,776,218 — Svensson
U.S. Pat. No. 3,788,305 — Schreiber

SUMMARY OF THE INVENTION

It is an object of the present invention to provide an apparatus for making experimental analyses on freely moving living animals such as birds, whales, and other mammals by taking blood, or other body fluid samples at predetermined pressures or times.

It is another object of the invention to provide an apparatus of the class described for obtaining in vivos samples of blood or other body fluids from animals moving in their natural environment. In this way, the influence on the animal of a false or unnatural sampling environment is totally eliminated.

It is still another object of the invention to provide an apparatus of the aforementioned character in which the fluid samples can be obtained and stored for future analysis at the same pressures at which they were obtained. In this way accurate analysis can be made of the nature, amount and partial pressure of dissolved gases disposed within the fluid samples withdrawn from the mammal.

It is another object of the invention to provide an apparatus as heretofore described which is highly versatile and can be used with minimum modification for a wide variety of experiments conducted on a wide variety of species.

It is another object of the invention to provide an apparatus as described which is of simple design, embodies a minimum number of component parts, provides high quality results, and is readily operable with simple and unsophisticated support systems.

It is a further object of the invention to provide an apparatus, as described, which is lightweight, easy to assemble and use, is extremely durable in operation, and yet can be inexpensively manufactured.

These and other objects of the invention are realized by an apparatus for withdrawing fluids from or injecting fluids into mammals comprising a hollow body having first and second chambers, the first chamber having a fluid medium therein at a first pressure and the second chamber having a fluid medium therein at a second pressure whereby a predetermined pressure differential exists between the first and second chambers; a piston carried within the first chamber for reciprocal movement therein; an elongated probe connected at one end to the body and having at the opposite end a reduced diameter portion adapted to be inserted into the mammal, the probe further including an axial bore extending therethrough in communication with the first chamber; and a frangible member disposed within the body intermediate the first and second chambers, the member normally blocking fluid flow between the chambers, but being breakable by a predetermined increase in pressure differential between the first and second chambers.

BRIEF DESCRIPTION OF THE DRAWINGS

FIG. 1 is a longitudinal sectional view of the apparatus of the invention illustrating the orientation of the component parts of the device as they appear immediately prior to the acquisition of a fluid sample from, for example, an aquatic mammal.

FIG. 2 is a cross sectional view taken along lines 2—2 of FIG. 1.

FIG. 3 is a foreshortened view similar to FIG. 1, but showing the position of the parts of the device during the actual withdrawal of the fluid sample from the mammal.

FIG. 4 is a view similar to FIG. 3 but showing the position of the parts at the completion of the withdrawal of the fluid sample.

FIG. 5 is a foreshortened longitudinal sectional view similar to FIG. 1 illustrating an alternate form of the invention specifically for use in the injection of fluids. In this figure the orientation of the component parts of the device are shown as they appear immediately prior to the injection of a fluid into, for example, an aquatic mammal.

FIG. 5a is a fragmentary cross sectional view of the check valve portion of the probe of the apparatus of FIG. 5.

FIG. 6 is a fragmentary view similar to FIG. 5 illustrating the rupture of the frangible disc to permit passage therethrough of the fluid to be injected.

FIG. 7 is a generally schematic view of a fluid pressurizing system for use with the apparatus of the invention.

DESCRIPTION OF ONE FORM OF THE INVENTION

Referring now to the drawings and particularly to FIGS. 1 and 2, there is shown the apparatus of the invention for the in viva injection of fluids into, or the withdrawal of body fluids from, living creatures such as birds, fish, whales, and other mammals. The apparatus comprises an elongated cylindrically hollow body 12 which is generally circular in cross section at any point and has disposed therewithin substantially cylindrically shaped first and second chambers 14 and 16 respectively, the precise configuration of which will presently be discussed. Body 12 is constructed of a noncorrosive material such as stainless steel, or the like, and is designed to withstand relatively high external pressures such as might be experienced at ocean depths of several hundred feet.

Contained within first chamber 14 is a fluid at a first pressure. Contained within second chamber 16 is a fluid at a second pressure. The nature of the fluids and their relative pressures vary depending upon whether the device is being used for the injection of fluids into the animal or the withdrawal of fluids, such as blood, therefrom.

The apparatus of the invention as illustrated in FIG. 1 is set up for use in the withdrawal of a fluid sample from a living creature as, for example, a whale or other mammal. When so used, the fluid in first chamber 14 is a silicone oil or other similar lightweight noncorrosive liquid medium. The fluid in chamber 16 is air or nitrogen at a pressure less than atmospheric.

Carried within first chamber 14 and adapted for reciprocal movement therewithin, is a generally cylindrically shaped piston 18. Sealing means are provided at the periphery of the piston for preventing the passage of fluids between piston 18 and the inner walls 20 of first chamber 14. In the embodiment of the invention shown in the drawings, the sealing means is provided in the form of an annular shaped "O" ring 22. Ring 22 is suitably constructed from a soft resilient material such as neoprene, rubber, or the like.

An elongated probe or catheter 24 comprising a shank portion 24a and a needle portion 24b, is removably connected to the forward end of body 12. The shank portion of the catheter is provided with threads which are receivable in an internally threaded aperture 26 formed in the forward wall of body 12. The middle portion of the catheter has a reduced diameter portion 28 proximate its forward end which is adapted to be inserted into the creature. An axial bore 30 is formed through the entire length of the catheter so that when the catheter is connected to the body, bore 30 is in open communication with first chamber 14.

To control the flow of fluids within axial bore 30, a pressure operated valve means is disposed within axial bore 30 intermediate the shank and needle portions of the catheter. In the embodiment shown in the drawings, the valve means is provided in the form of a ball check valve 32. Ball check valve 32 is of standard construction having a spherical member 34 which is urged into closing engagement with bore 30 by a biasing means or spring 36. With this construction, whenever the pressure of the fluid within the needle portion of the catheter exceeds a predetermined amount, sphere 34 will be urged rearwardly (to the right in FIG. 1) permitting the flow of the fluid through bore 30 into first chamber 14.

Disposed within body 12 intermediate first and second chambers 14 and 16 is a frangible means shown here in the form of a frangible disc 38. Disc 38 is adapted to normally prevent fluid flow from chamber 14 into chamber 16, but is designed to rupture when the pressure differential between the first and second chambers exceeds a predetermined amount. The frangible disc can be constructed from a wide variety of materials including thin metal foil, plastic, and various types of composite materials. The material selected, its thickness and its strength varies depending upon the application to be made of the apparatus and the rupture characteristics desired.

Located intermediate first chamber 14 and frangible disc 38 is a fluid pressure focusing means for focusing upon disc 38 pressure exerted by the fluid contained within first chamber 14. In the embodiment here illustrated, the pressure focusing means is provided in the form of an annular shaped member 40 which is in sealable engagement at its rearward face with the frangible disc 38 and at its periphery with the inner walls 20a of body 12. Providing a seal between member 40 and frangible disc 38 is an annular shaped rubber or neoprene "O" ring 42. Providing a seal between member 40 and the inner walls 20a of body 12 is a rubber or neoprene "O" ring 44. "O" rings 42 and 44 are of a construction similar to that of "O" ring 22 as previously described and are adapted to prevent the flow of fluid from chamber 14 around the periphery and the rearward face of member 40. The central portion of annular member 40 defines a fluid passageway 46 which is in open communication with chamber 14 at its forward end and is normally closed at its rearward end by frangible disc 38.

With the construction thus described, fluid contained in chamber 14 exerts forces upon disc 38 in a central area defined by the cross-sectional area of passageway 46. Passageway 46 also serves the important function of metering the sample to preclude breakdown of red corpuscles. It is to be noted that the forward face of member 40 defines a piston engaging shoulder 48 adapted to limit the extent of rearward motion of piston 18 within chamber 14.

At the rearward extremity of body 12 there is provided closure means for sealing second chamber 16 relative to atmosphere. In the form of the invention shown in the drawings, the closure means comprises in combination a threaded clean-out plate 50 and a threaded pressure seal cap 52. Both members 50 and 52 are provided with spanner wrench apertures 54 and are adapted to be threadably received within an internally threaded portion 30b of body 12. A spacer ring 54 is provided intermediate frangible disc 38 and member 50 to limit the extent of forward travel of member 50. Member 50 and spacer ring 54 are provided with centrally disposed generally cylindrically shaped passageways 56 and 58 respectively which passageways together comprise second chamber 16.

A threaded plug 60 is threadably received within a threaded bore 61 provided in member 52. Removal of plug 60 provides access to chamber 16 to enable evacuation or pressurization thereof. Member 52 is also provided with a flanged portion 62 which is adapted to sealably engage a neoprene or rubber "O" ring 64 carried within an "O" ring groove formed within flanged portion 66 of body 12.

OPERATION

When the apparatus of the invention is to be used for withdrawing from the animal liquid specimens such as blood, the device is assembled in the following manner: First, the shank portion 24a of the probe or catheter is threadably connected to the forward portion of housing 12. Piston 18 is then inserted into first chamber 14 through the rearward open end of body 12 and moved forwardly to a position proximate the forward end of the body. Next, annular member 40 is inserted into body 12 and moved forwardly into engagement with shoulders 68 formed interiorly of body 12. With the parts thus assembled a fluid such as silicone oil is introduced into the assembly until it fills chamber 14 and passageway 46 of member 40. Frangible disc 38 is then introduced through the rearward open end of the body and moved into engagement with member 40. Next, spacer ring 54 is inserted into the body and positioned against frangible disc 38. Clean-out plate 50 is then threaded into the body using a suitable spanner wrench and is snugged down against spacer 54. Using the spanner wrench, pressure seal cap 62 is then threaded into the rearward portion of body 12 and moved into sealable engagement with "O" ring 64. Plug 60 is then removed and second chamber 16 comprising passageways 56 and 58 is evacuated. Finally, plug 60 is replaced to seal the assembly relative to atmosphere.

The assembled apparatus is then ready to be attached to the mammal or other animal from which the sample is to be taken. This is done by inserting end 28 of the catheter into, for example, a vein or artery of the animal and then securely affixing the apparatus to the animal using straps or any other suitable fastening means.

The animal with the apparatus attached is free to move about in its natural environment. In the form of the invention shown in the drawings, withdrawal of the sample takes place when there is a change in fluid pressure in the catheter. For example, if the apparatus is being used to obtain a sample of blood from an aquatic animal such as a whale, diving by the whale to a predetermined depth would cause an increase in its blood pressure. This in turn would cause an increase in the pressure of the blood within the catheter bore urging movement of piston 18 rearwardly within chamber 14 to a position shown in FIG. 3. Rearward movement of the piston tends to compress the silicone oil which in turn causes an increase in the fluid pressure being exerted on frangible disc 38. When a predetermined amount of pressure is exerted on the frangible disc, the central portion thereof will fail in the manner shown in FIG. 3. This opens communication between chambers 14 and 16. Due to the reduced pressure in chamber 16, piston 18 will then move rapidly rearwardly to the position shown in FIG. 4. This rearward movement of piston 18 permits that portion of first chamber 14 which is forwardly of the piston to fill with blood. When the chamber is filled with blood and the pressure equalizes, check valve 32 will close sealing the sample within the apparatus. The integrity of the sample and any gases trapped therein will thusly be maintained until the apparatus is recovered.

When the apparatus is to be used for injecting fluids, the device is assembled in the following manner: Prior to threadably connecting the catheter 24 to the body portion 12, piston 18 is positioned in the rearwardmost portion within first chamber 14, that is, into the position of the piston shown in FIG. 4. The portion of chamber 14 forwardly of the piston is then filled with the fluid to be injected as, for example, anesthetic. This done, the probe or catheter is threadably connected to the body portion 12. For this application of the apparatus the catheter is of a slightly different design, the check valve portion thereof being reversed from the configuration shown in FIG. 1. In other words, in this design the spherical member 34 seats against the forward opening of the bore 30a provided in shank portion 24a. Spring 36 is also reversed from the position shown in FIG. 1 so that it continually urges sphere 34 into sealing engagement with the forward end of bore 30a. For reference purposes, the position of the parts of the check valve for this application is similar to that shown in FIG. 5a.

With the piston in the rearwardmost portion within first chamber 14, elements 40, 38, 54, 50, and 52 are inserted into body 12 and located in the manner previously described. In place of plug 60, however, there is inserted a fitting 70 (FIG. 7) interconnected with a source of fluid under pressure. This may be, for example, a compressed gas cylinder 72 or other vessel containing liquid such as oil under pressure. Disposed intermediate fitting 70 and cylinder 72 is a normally closed valve 74. Valve 74 is operable by a valve actuation means 76 which is operably interconnected with the valve. Means 76 may be triggered, for example, by a timer 78. Alternating means 76 may be triggered by an electrical signal, by sonic means, or by a pressure sensitive device. The valve, valve actuation means and triggering means use shown schematically in FIG. 7, but are components well known in the art. Neither the components nor their manner of interconnection form a part of the present invention and, therefore, will not be discussed in detail.

After the apparatus has been assembled in the manner described, the catheter is inserted into the animal and the apparatus affixed to the animal by straps or the like. At a predetermined time, or under predetermined pressure conditions, timer 78, or an alternate type of triggering means, triggers valve actuation means 76 which in turn opens valve 74. This permits fluid under pressure to flow into chamber 16. This fluid pressure is of sufficient magnitude to cause frangible disc 38 to rupture, opening comunication between chambers 16 and 14 and permitting the fluid under pressure to flow into chamber 14 and into passageway 46. The fluid pressure is rearward face of piston 18 causing the piston to move forwardly within chamber 14. Forward movement of the piston urges the fluid within chamber 14 into bore 30a of the catheter causing the check valve 32 to open so that the fluid can be injected into the animal.

It is to be appreciated that the apparatus of the embodiment of the invention, as described in the preceeding paragraphs, can be used singly or, where more than one sample is to be taken, any number of units can be interconnected to a manifold provided with a common catheter through which the samples can be obtained. Similarly, for certain applications, a plurality of catheters can be connected to a common manifold which in turn is connected with the apparatus of the invention. Additionally, although the apparatus for obtaining samples as shown in the drawings is pressure activated, the device can easily be modified by those skilled in the art to be actuated by a timer, by an electrical signal, or by sonic means.

DESCRIPTION OF THE ALTERNATE FORM OF THE INVENTION

An alternate form of the apparatus of the invention for the in viva injection of fluids into animals is illustrated in FIGS. 5 and 6. Referring particularly to FIG. 5, the apparatus of this embodiment comprises a hollow body 75 having disposed therewithin substantially cylindrically shaped first and second chambers 77 and 79 respectively. Contained in first chamber 77 is the fluid to be injected, for example, an anesthetic at a first pressure. Contained within the second chamber 79 is a fluid medium such as silicone oil at a second pressure.

A catheter 81 of the same general construction as that previously described in connection with the embodiment of the invention shown in FIGS. 1 through 4 is threadably connected to body 75 at its forward end. Catheter 81 is adapted to be inserted into the animal and has a fluid passageway 83 (FIG. 5a) therethrough which is in operable communication with a fluid outlet passageway 85 formed in body 75 and communicating with first chamber 77.

A frangible disc 87 is disposed within body 75 between first chamber 77 and outlet passageway 85. Disc 87 normally prevents fluid flow from first chamber 77 into outlet passageway 85. The disc will, however, be ruptured by the exertion thereupon of a predetermined amount of fluid pressure.

Carried within first chamber 77 is a first piston 89 adapted for reciprocal movement within chamber 77. An "O" ring 91 is carried within a groove formed in the periphery of piston 89 and functions to provide a seal between the piston and the inner wall 93a of chamber 77. "O" ring 91, which is of similar construction to the "O" rings previously described, functions to prevent fluid flow between the piston and the inner walls of chamber 77 as the piston reciprocates therewithin. Carried within second chamber 79 is a second piston 95 which is adapted for reciprocal movement therewithin.

An "O" ring 97 is carried within a groove formed within the periphery of piston 95. "O" ring 97 functions to prevent the flow of fluid between the periphery of piston 95 and the inner wall 99 of chamber 77.

Disposed intermediate chambers 77 and 79 is a fluid focusing means shown in the drawings in the form of an annular shaped member 101. The central portion of member 101 defines a fluid passageway 103. Carried at the forward extremity of body 75 and disposed proximate frangible disc 87 is an annular shaped spacer member 105, the purpose of which will be presently described.

Closure means provided in the form of a closure plate 107 is threadably received within the rearwardly open internally threaded portion of body 75. Closure member 107 is provided with a flange portion 107a which is adapted to pressurally engage an "O" ring 109 carried within an "O" ring groove formed in the rear wall 111 of body 75. Closure plate 107 is provided with spanner wrench apertures 113 and a fluid inlet passageway 115 adapted to permit the introduction of fluids under pressure into second chamber 79.

OPERATION OF ALTERNATE FORM

The apparatus of this form of the invention is assembled in the following manner. First, the shank portion 81a of the catheter (FIG. 5a) is threadably connected to the forward portion of housing 75. With "O" ring 88 in position within the "O" ring groove formed in the forward wall 75a of housing 75, frangible disc 87 is introduced through the open rearward end of the housing and is seated against "O" ring 88. Annular member 105 is then inserted into the body and moved into engagement with frangible disc 87. Next, chamber 77 is partially filled with the fluid to be injected. Piston 89 is then inserted into the body portion so that the fluid is encapsulated within the body between the frangible disc 87 and the forward face of piston 89. Annular member 101 is then inserted into the body and moved into engagement with piston 89. A viscous liquid such as silicone oil is then added to the assembly so that it fills passageway 103 in member 101 and partially fills second chamber 79. This done, piston 95 is inserted into the rearward portion of chamber 79. Finally, the rearward end of body 75 is closed by threadably inserting closure member 107 using suitable spanner wrench.

After the apparatus has been assembled in the manner described, catheter 81 is inserted into the animal and the apparatus affixed to the animal by straps or the like. Depending upon the application to be made of the apparatus, there is inserted into passageway 115 a fitting such as fitting 70 shown in FIG. 7. Fitting 70 is interconnected with the source of fluid under pressure such as, for example, a compressed gas cylinder 72. Disposed intermediate fitting 70 and cylinder 72 is a normally closed valve 74. As earlier described valve 74 is operable by a valve actuating means 76 which is triggered by a triggering means as, for example, a timer 78.

Once the apparatus is affixed to the animal, the animal is released and permitted to move about freely in its natural environment. At a predetermined time, or under predetermined pressure conditions, timer 78, or an alternate type of triggering means, triggers valve actuation means 76 which in turn opens valve 74. This permits fluid under pressure to flow into chamber 79 urging piston 95 forwardly within chamber 79. Forward movement of piston 95 causes fluid pressure to act through passageway 103 against the rearward face of piston 89.

This pressure causes piston 89 to move forwardly within chamber 77 forcing the fluid to be injected through central passageway 105a of member 105 thereby exerting a focused fluid pressure upon frangible disc 87. At a predetermined pressure, disc 87 will rupture permitting the fluid to flow into bore 83 of the catheter through outlet passageway 85. Pressure exerted on the fluid causes the check valve to open so that the fluid can be injected into the animal.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A pressure sensitive device for withdrawing fluids from or injecting fluids into mammals comprising:
    a. a hollow body including first and second chambers, said first chamber having a fluid medium therein at a first pressure and said second chamber having a fluid medium therein at a second pressure whereby a predetermined pressure differential exists between said first and second chambers;
    b. a piston carried within said first chamber for reciprocal movement therein;
    c. an elongated probe connected at one end to said body and having at the opposite end a reduced diameter portion adapted to be inserted into the mammal, said probe being provided with an axial bore extending therethrough in communication with said first chamber; and
    d. frangible means disposed within said body intermediate said first and second chambers, said means normally blocking fluid flow between said chambers, but being rupturable by a predetermined increase in pressure differential between said first and second chambers.

2. The device as defined in claim 1 further including an annular shaped member disposed within said hollow body intermediate said frangible means and said first chamber. Said member being in sealable engagement with said frangible means and defining a fluid passageway which is in communication with said first chamber at one end, and which is normally closed at its other end by said frangible means.

3. The device as defined in claim 1 including first sealing means carried by said piston for preventing the passage of fluids between said piston and the walls of said first chamber as said piston reciprocates within said first chamber.

4. The device as defined in claim 1 including means for varying the pressure of the fluid medium within said second chamber.

5. The device as defined in claim 1 including pressure operated valve means disposed within the axial bore of said probe for regulating the flow of fluid therethrough.

6. An apparatus for the in viva acquisition of fluid samples from creatures such as birds, fish, whales, and other mammals comprising:
    a. a hollow body defining substantially cylindrically shaped first and second chambers, said first chamber having a fluid therein and said second chamber having at least a partial vacuum therein;
    b. a piston carried within said first chamber in sealable engagement with the internal wall of said body and adapted for movement within said first chamber in a direction toward said second chamber;
    c. a catheter connected to said hollow body, said catheter being adapted to be inserted into a fluid carrying body vessel of the creature and having a fluid passageway therethrough in operable communication with said first chamber; and
    d. a frangible disc disposed within said body intermediate said first and second chambers, said disc normally preventing fluid flow from said first chamber into said second chamber, but being rupturable by a predetermined increase in pressure differential between said first and second chambers caused by movement of said piston toward said second chamber.

7. The apparatus as defined in claim 6 including pressure focusing means interposed between said first chamber and said frangible disc for focusing upon said disc pressure exerted thereupon by the fluid in said first chamber upon movement of said piston in a direction toward said second chamber and for metering fluid flow toward said frangible disc.

8. The apparatus as defined in claim 7 in which said pressure focusing means comprises an annular shaped member disposed within said body in sealable engagement therewith said member including a piston engaging shoulder adapted to limit the movement of said piston within said first chamber.

9. An apparatus for the in viva injection of fluids into creatures such as birds, fish, whales, and other mammals comprising:
    a. a hollow body defining substantially cylindrically shaped first and second chambers, said first chamber having therein at a first pressure the fluid and said second chamber having therein a fluid at a second pressure;
    b. a piston carried within said first chamber in sealable engagement with the internal wall of said body and adapted for movement within said first chamber in a direction away from said second chamber;
    c. a catheter connected to said hollow body, said catheter being adapted to be inserted into the creature and having a fluid passageway therethrough in operable communication with said first chamber; and
    d. a frangible disc disposed within said body intermediate said first and second chambers, said disc normally preventing fluid flow from said first chamber into said second chamber, but being rupturable by a predetermined increase in pressure differential between said first and second chambers caused by movement of said piston toward said second chamber.

10. The apparatus as defined in claim 9 in which the fluid in said first chamber is an anesthetic and the fluid in said second chamber is a silicone oil.

11. An apparatus for the in viva injection of fluids into or the withdrawal of body fluids from living creatures such as birds, fish, whales, and other mammals comprising:
    a. a hollow body defining substantially cylindrically shaped first and second chambers, said first chamber having a fluid therein at a first pressure and said second chamber having therein a fluid at a second pressure;
b. a piston carried within said first chamber and adapted for reciprocal movement therewithin;
c. first sealing means carried by said piston for preventing the passage of fluids between said piston and the walls of said first chamber as said piston moves therewithin;
d. a catheter connected to said hollow body, said catheter being adapted to be inserted into the creature and having a fluid passageway therethrough in operable communication with said first chamber;
e. a frangible disc disposed within said body intermediate said first and second chambers, said disc normally preventing fluid flow from said first chamber into said second chamber, but being rupturable by a predetermined increase in pressure differential between said first and second chambers;
f. an annular shaped member disposed within said hollow body intermediate said frangible disc and said first chamber, said member being in sealable engagement with said frangible disc and with the inner walls of said body and defining a fluid passageway which is in open communication with said first chamber at one extremity and is normally closed at its opposite extremity by said frangible disc; and
g. closure means removably connected to said body proximate said second chamber for sealing said second chamber relative to external atmosphere.

12. The apparatus as defined in claim 11 in which said closure means is provided with a sealable passageway leading to said second chamber for the introduction or withdrawal of fluids therefrom.

13. An apparatus for the in viva injection of fluids into creatures such as birds, fish, whales, and other mammals comprising;
a. a hollow body defining substantially cylindrically shaped first and second chambers, said first chamber having therein the fluid to be injected at a first pressure and said second chamber having therein a fluid at a second pressure;
b. a catheter connected to said hollow body, said catheter being adapted to be inserted into the creature and having a fluid passageway therethrough in operable communication with a fluid outlet passageway formed in said body and communicating with said first chamber;
c. a frangible disc disposed within said body between said first chamber and said outlet passageway, said disc normally preventing fluid flow from said first chamber into said outlet passageway, but being rupturable by a predetermined increase in fluid pressure exerted thereon by the fluid in said first chamber.
d. a first piston carried within said first chamber and adapted for movement therewithin; in a direction toward said frangible disc;
e. a second piston carried within said second chamber and adapted for movement therewithin in a direction toward said first piston; and
f. closure means removably connected to said body proximate said second chamber for substantially closing one end of said second chamber, said closure means having a fluid, inlet passageway therein adapted to permit the introduction of fluids under pressure into said second chamber.

* * * * *